United States Patent
Park et al.

(10) Patent No.: US 9,962,240 B2
(45) Date of Patent: May 8, 2018

(54) DENTAL IMPLANT FIXTURE (75) Inventors: Sang Oh Park, Busan (KR); Byung Kook Kim, Busan (KR); Mu Young Park, Busan (KR); Tae Gwan Eom, Busan (KR); Kyoo Ok Choi, Seoul (KR)

(73) Assignee: OSSTEMIMPLANT CO., LTD., Seoul (KR)

( * ) Notice: Subject to any disclaimer, the term of this patent is extended or adjusted under 35 U.S.C. 154(b) by 423 days.

(21) Appl. No.: 12/993,142

(22) PCT Filed: May 19, 2009

(86) PCT No.: PCT/KR2009/002637
§ 371 (c)(1),
(2), (4) Date: Nov. 17, 2010

(87) PCT Pub. No.: WO2009/142429
PCT Pub. Date: Nov. 26, 2009

(65) Prior Publication Data
US 2011/0070558 A1    Mar. 24, 2011

(30) Foreign Application Priority Data
May 19, 2008 (KR) .................. 10-2008-0046158

(51) Int. Cl.
*A61C 8/00* (2006.01)
*A61B 17/86* (2006.01)

(52) U.S. Cl.
CPC .......... *A61C 8/0022* (2013.01); *A61B 17/863* (2013.01); *A61C 8/0025* (2013.01); *A61B 17/864* (2013.01); *A61B 17/8635* (2013.01)

(58) Field of Classification Search
CPC . A61B 17/863; A61B 17/8635; A61B 17/864; A61C 8/0022; A61C 8/00; A61C 8/0025
(Continued)

(56) References Cited

U.S. PATENT DOCUMENTS 4,863,383 A * 9/1989 Grafelmann ....... A61B 17/8625
433/174
5,199,873 A * 4/1993 Schulte et al. ................ 433/174
(Continued)

FOREIGN PATENT DOCUMENTS

KR      20-0424914 Y1    8/2006

OTHER PUBLICATIONS

International Search Report: PCT/KR2009/002637.

*Primary Examiner* — Cris L Rodriguez
*Assistant Examiner* — Mirayda A Aponte
(74) *Attorney, Agent, or Firm* — Ladas & Parry LLP (57) ABSTRACT

The present invention relates to a dental implant fixture, and more particularly, to a dental implant fixture which rotates about a central axis thereof, and thus is inserted into a bone tissue constituted by a cortical bone and a spongy bone to form an artificial tooth root, wherein the dental implant fixture includes a first portion, a second portion, and a third portion. The first portion is inserted into the cortical bone and has an outer surface with a first screw thread whereon first vertices and first valleys are alternately arranged. The second portion is disposed beneath the first portion and inserted into the spongy bone, has an outer surface with a second screw thread whereon second vertices and second valleys are alternately arranged. The distance between the adjacent second vertices of the second screw thread is larger than the distance between the adjacent first vertices of the first screw thread. The third portion is disposed beneath the second portion, and has an outer surface with a third screw thread whereon third vertices and third valleys are alternately arranged, and a first cutting part which is hollowed such that the first cutting part is closer to the central axis than the third valleys. The lower outer diameter of the second (Continued)

screw thread is smaller than the upper outer diameter of the second screw thread.

17 Claims, 8 Drawing Sheets

(58) Field of Classification Search
 USPC .............................. 433/165, 173–176, 201.1
 See application file for complete search history.

(56) References Cited

U.S. PATENT DOCUMENTS

| | | | | |
|---|---|---|---|---|
| 5,749,732 | A * | 5/1998 | Sendax | A61C 8/0089 |
| | | | | 433/174 |
| 6,585,740 | B2 * | 7/2003 | Schlapfer | A61B 17/863 |
| | | | | 411/380 |
| 7,172,416 | B2 * | 2/2007 | Lin | A61C 7/00 |
| | | | | 433/174 |
| 7,396,231 | B2 * | 7/2008 | Niznick | 433/173 |
| 7,597,557 | B2 * | 10/2009 | Fromovich et al. | 433/174 |
| 7,677,891 | B2 * | 3/2010 | Niznick | 433/174 |
| 2004/0006346 | A1 | 1/2004 | Holmen et al. | |
| 2004/0121289 | A1 * | 6/2004 | Miller | A61C 8/0022 |
| | | | | 433/174 |
| 2004/0146834 | A1 * | 7/2004 | Haessler | 433/174 |
| 2004/0219488 | A1 * | 11/2004 | Choi et al. | 433/173 |
| 2005/0250074 | A1 * | 11/2005 | Lang et al. | 433/174 |
| 2006/0147880 | A1 * | 7/2006 | Krumsiek et al. | 433/174 |
| 2006/0172258 | A1 * | 8/2006 | Niznick | 433/174 |
| 2007/0099153 | A1 * | 5/2007 | Fromovich | A61C 8/0022 |
| | | | | 433/174 |
| 2008/0081316 | A1 * | 4/2008 | Chung | A61C 8/0075 |
| | | | | 433/174 |
| 2008/0145819 | A1 * | 6/2008 | Boettcher | A61C 8/0025 |
| | | | | 433/174 |
| 2008/0160483 | A1 * | 7/2008 | Danger et al. | 433/174 |
| 2010/0304335 | A1 * | 12/2010 | Garcia Saban et al. | 433/174 |
| 2010/0330534 | A1 * | 12/2010 | Hyun | 433/174 |
| 2011/0008753 | A1 * | 1/2011 | Rupprecht et al. | 433/173 |
| 2012/0015325 | A1 * | 1/2012 | Chen | 433/174 |
| 2012/0021381 | A1 * | 1/2012 | Hurson | 433/174 |
| 2012/0237898 | A1 * | 9/2012 | Palti et al. | 433/174 |
| 2012/0264084 | A1 * | 10/2012 | Hansson et al. | 433/174 |

* cited by examiner

FIG. 1

—Prior Art—

DENTAL IMPLANT FIXTURE

TECHNICAL FIELD

The present invention relates to relates to an implant fixture, and more particularly, to a dental implant fixture that achieves initial fixing force even when inserted into a soft bone tissue like cancellous bone and reduces a time for osseointegration between the dental implant fixture and peripheral bones.

BACKGROUND ART

A screw type implant fixture includes a body having a screw thread formed on an outer surface and is used as a fixing unit to fix a dental or orthopedic prosthesis or the like into a bone. A bone tissue into which a fixture is to be inserted consists of cancellous and cortical bones. The cancellous bone refers to a relatively soft bone tissue of a bone, and the cortical bone refers to a relatively thin film, which is harder than the cancellous bone and generally encloses the cancellous bone. A length of the cancellous bone is usually longer than the cortical bone and thus the inserted fixture is implanted into the cancellous bone.

Figure 1:
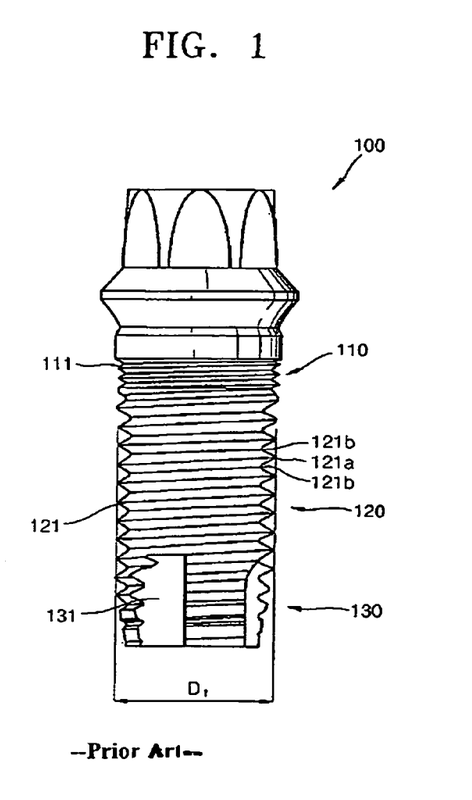
FIG. 1 illustrates an implant fixture according to the conventional art.

FIG. 1 illustrates an implant fixture 100 according to the conventional art. The implant fixture 100 includes a second portion 120 having a large screw thread 121 including peaks 121a and roots 121b alternating with one another on a central axis of the implant fixture 100, a first portion 110 disposed above the second portion 120 and including a smaller screw thread 111 than the screw thread 121 of the second portion 120, and a third portion 130 disposed below the second portion 120 and including a cave cutting portion 131 on the central axis of the implant fixture 100. A depth of a cave of the cave cutting portion 131 is longer than the bone of the third portion 130 so that the cave cutting portion 131 enables the implant fixture 100 to be easily inserted into a bone tissue at an initial stage. Also, outer diameters D1 of the first portion 110 and the second portion 120 are the same along the central axis.

The implant fixture 100 is inserted into an implant hole formed in a bone tissue of the human body using a drill. When the implant fixture 100 is inserted into the bone tissue, the third portion 130 and the first portion 110 are sequentially implanted into a cancellous bone, and the first portion 110 is implanted into a cortical bone. After the implantation is completed, bone tissues near the implant fixture 100 are grown to integrate with a surface of the implant fixture 100 to thereby fix the implant fixture 100.

However, the implant fixture 100 according to the conventional art has the following drawbacks.

First, the second portion 120 of the implant fixture 100 is not inserted into the bone tissue by sufficiently applying a pressure to the bone tissue, and thus the implant fixture 100 does not have a sufficient initial fixing force when the implantation is completed. Thus, bone absorption may occur near the implant fixture 100. The bone absorption is an atrophy due to a reduction in the amount of a bone tissue near the implanted implant fixture 100, which deteriorates the fixing force of the implant fixture 100, thereby hindering the whole stability of the implant fixture 100 or damaging a prosthesis attached to an upper end of the implant fixture 100.

Second, when a large implant hole is formed before the implant fixture 100 is inserted, osseointegration takes a long time and the initial fixing force is likely deteriorated as well. More specifically, such a large implant hole causes a bone tissue near the implant fixture 100 and the surface thereof to be far away from each other, which increases the amount of the bone tissue to be grown on the surface of the implant fixture 100, thereby increasing the total time for osseointegration.

Third, when an implant hole is not formed using a drill in a desired direction in a straight manner before the implant fixture 100 is implanted, if a thread has a stumpy peak cross section as shown in the conventional art, the implant fixture 100 is implanted in a wrong direction. More specifically, the implant fixture 100 follows a direction of the implant hole and has difficulties in changing a direction thereof to a desired direction or moving a position thereof. When the implant fixture 100 is implanted in a wrong position, it is necessary to remove the implant fixture 100 from the wrong position, form a new implant hole, and insert the implant fixture 100 into the new implant hole.

DETAILED DESCRIPTION OF THE INVENTION

Technical Problem

The present utility model provides a dental implant fixture capable of achieving initial fixing force in a cancellous bone, preventing bone absorption after implantation, and being inserted into a desired direction.

Technical Solution

According to an aspect of the present invention, there is provided a ~~

Advantageous Effects

According to the dental implant fixture of the present invention described above, an outer diameter of a second screw thread implanted into a cancellous bone increases toward an upper side thereof, thereby achieving initial fixing force by applying a pressure to a bone tissue near the cancellous bone, and accordingly, preventing bone absorption after implantation.

The dental implant fixture formed with screw threads has a sharp cross section as a whole, so that the dental implant fixture can be inserted in a desired direction even when an implant hole is erroneously formed using a drill, thereby preventing a re-surgical operation.

BRIEF DESCRIPTION OF THE DRAWINGS

The above and other features and advantages of the present utility model will become more apparent by describing in detail exemplary embodiments thereof with reference to the attached drawings in which.

BEST MODE

Exemplary embodiments of the present utility model will now be described in detail with reference to the attached drawings.

Figure 2:
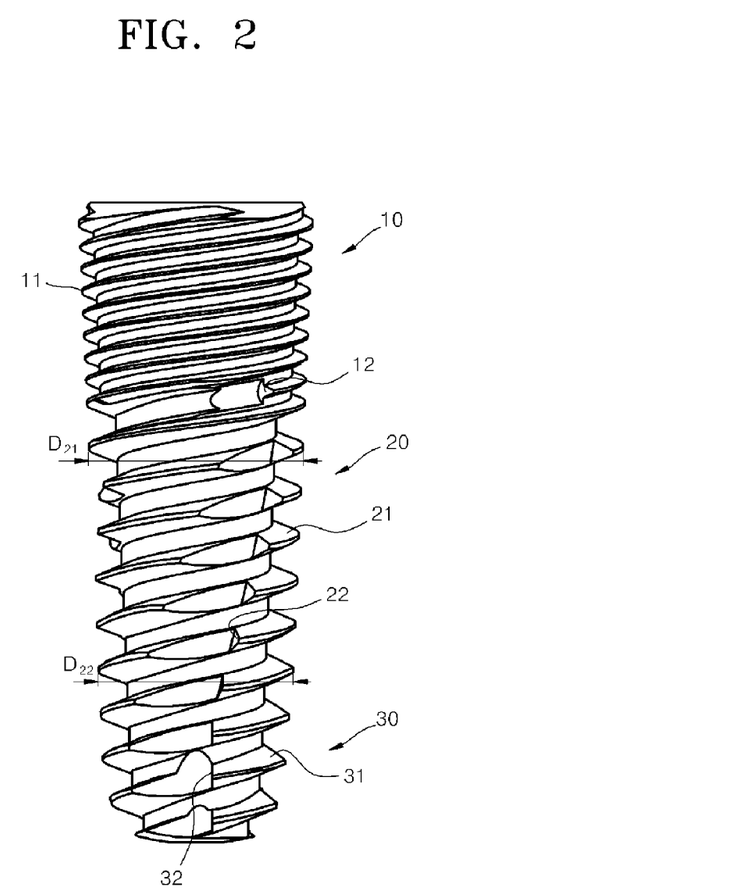
FIG. 2 illustrates an implant fixture according to an embodiment of the present invention.
Figure 3:
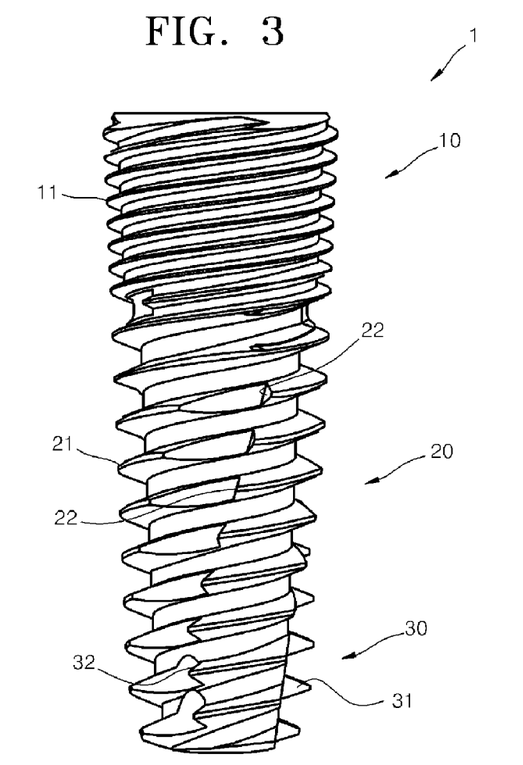
FIG. 3 illustrates the implant fixture of FIG. 2 viewed at a different angle.
Figure 4:
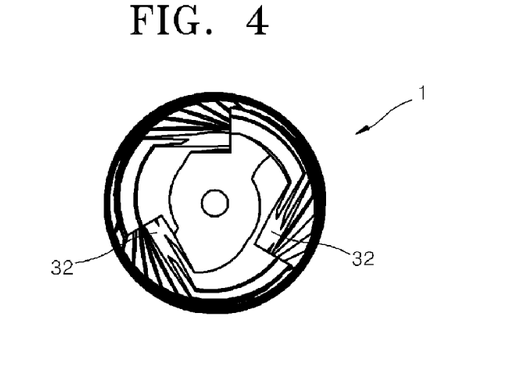
FIG. 4 is a rear view of the implant fixture of FIG. 2.
Figure 5:
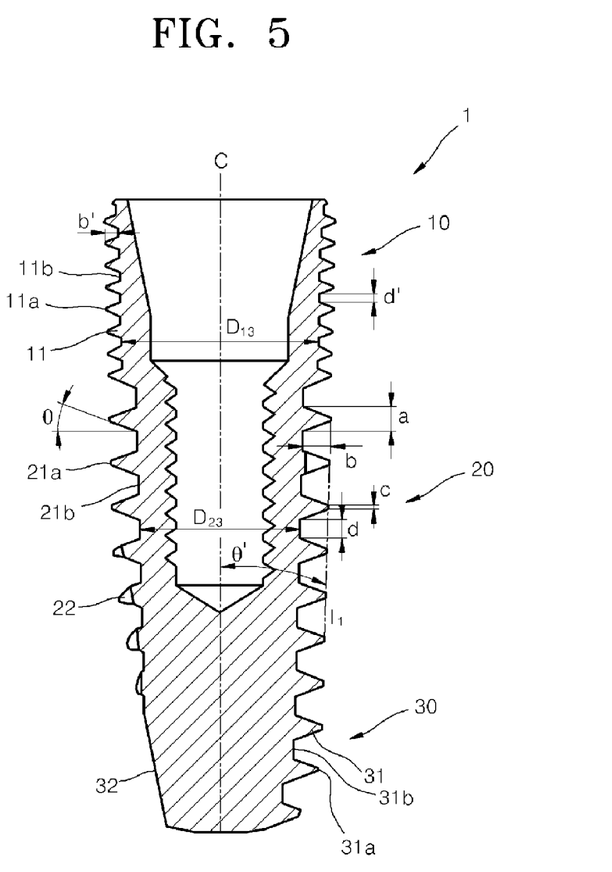
FIG. 5 is a cross-sectional view of the implant fixture of FIG. 2.
Figure 6:
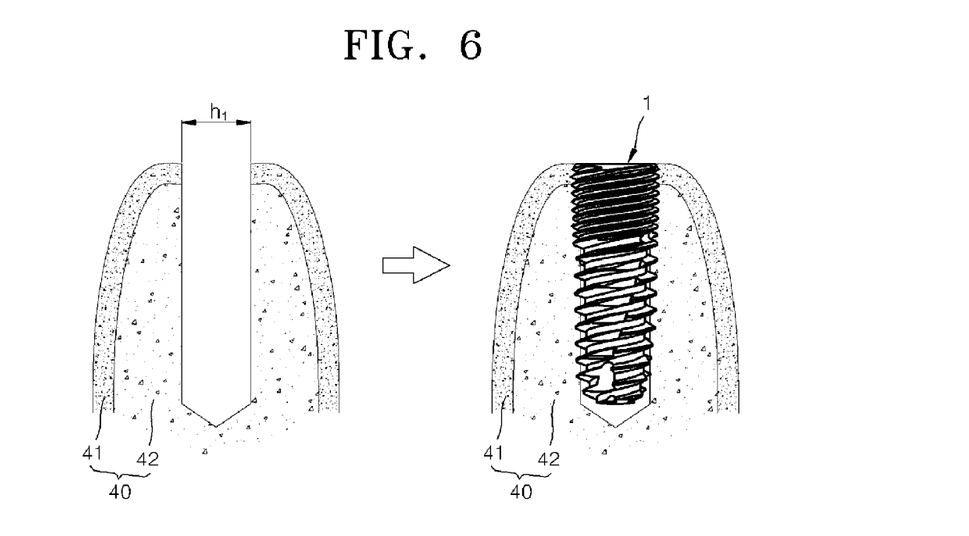
FIGS. 6 through 8 are schematic views illustrating the implant fixture of FIG. 2, being implanted into a bone tissue.
Figure 7:
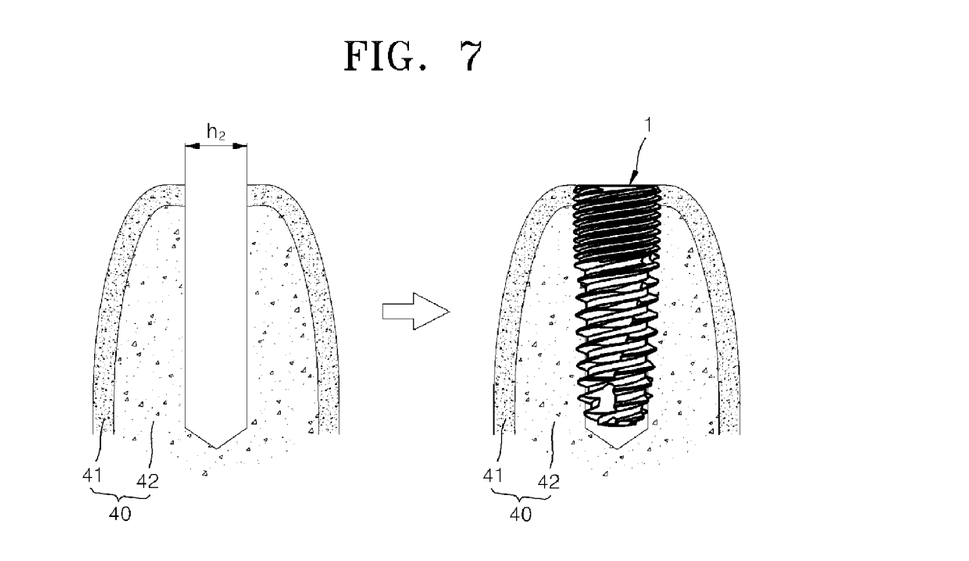
Figure 8:
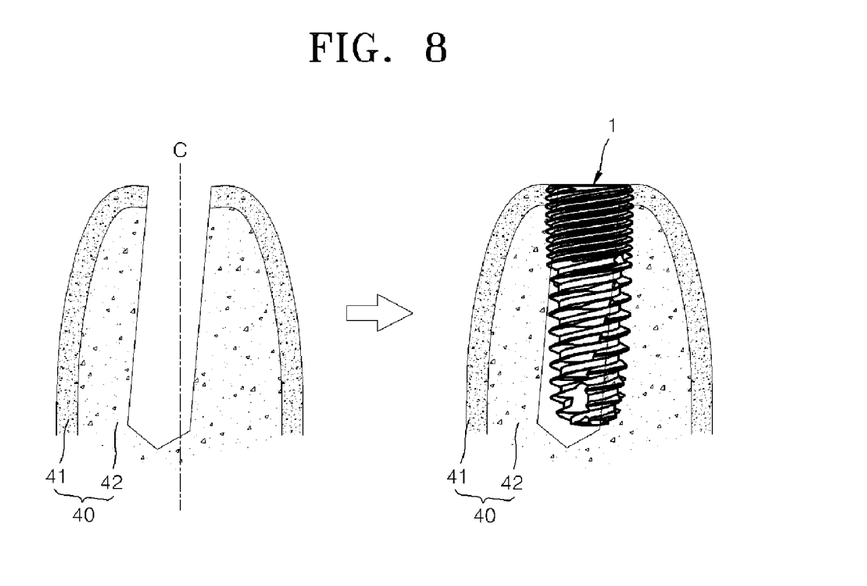

FIG. 2 illustrates an implant fixture 1 according to an embodiment of the present invention. FIG. 3 illustrates the implant fixture 1 of FIG. 2, viewed at a different angle. FIG. 4 is a rear view of the implant fixture 1 of FIG. 2. FIG. 5 is a cross-sectional view of the implant fixture 1 of FIG. 2. FIGS. 6 through 8 are schematic views illustrating the implant fixture 1 of FIG. 2, being implanted into a bone tissue 40.

The implant fixture 1 of the present embodiment is inserted into the bone tissue 40 consisting of a cortical bone 41 and a cancellous bone 42 so as to form an artificial tooth root. The implant fixture 1 has a cylindrical shape and an outer surface on which a screw thread is formed. When the implant fixture 10 rotates about a central axis C, the implant fixture 1 is inserted into the cortical bone 41 and the cancellous bone 42 to form screw roots at an inner surface of an implant hole formed in a bone tissue using a drill in advance. The implant fixture 1 may be formed of titanium or any other type of metal material that is not rejected by the human body.

The implant fixture 1 includes a first portion 10, a second portion 20, and a third portion 30.

The first portion 20 refers to a portion of the implant fixture 1 that is mostly inserted into the cortical bone 41 when the implant fixture 1 is inserted (the first portion 20 may also be partially implanted into the cancellous bone 42), and forms an upper side of the implant fixture 1. A first screw thread 11 is formed on an outer surface of the first portion 10. The first screw thread 11 has a spiral form, and includes first peaks 11a and first roots 11b alternating with one another in a direction of the central axis C.

In this regard, a screw thread disposed in the lowest end of the first screw thread 11 may have a cutting surface 12 approximately in parallel to a plane including the central axis C. The cutting surface 12 can be inclined toward the plane within about 30°.

More specifically, the number of screw lines of the first portion 10 increases, compared to that of the second portion 20, and thus a new screw thread is generated at a starting portion of the first screw thread 11. The conventional newly generated screw thread has a gradual protruding shape, which increases a cutting resistance in a process of inserting an implant fixture and thus a cutting becomes generally difficult. However, in the present embodiment, the cutting surface 12 formed in the lowest end of the first portion 10, which is an initial portion of the first screw thread 11, can facilitate cutting.

The second portion 20 is disposed below the first portion 10. In detail, the second portion 20 is integrally coupled to the first portion 20. However, the present invention is not limited thereto, and another structure may be disposed therebetween. Most of the second portion 20 is inserted into the cancellous bone 42 (a part of the second portion 20 may also be implanted into the cortical bone 41), thereby forming a lower portion of the implant fixture 10. A second screw thread 21 is formed on an outer surface of the second portion 20. The second screw thread 21 has a spiral form. The second screw thread 21 includes second peaks 21a and second roots 21b that alternate with one another in the direction of the central axis C. Distances (pitches; $S_2$) between the adjacent second peaks 21a of the second screw thread 21 are greater than distances (pitches; $S_1$) between the adjacent first peaks 11a of the first screw thread 11. That is, the cross-sectional size of the second screw thread 21 is greater than that of the first screw thread 11, and thus the second screw thread 21 is referred to as a 'macro-screw thread'. On the other hand, the cross-sectional size of the first screw thread 11 is smaller than that of the second screw thread 21 and thus is referred to as a 'micro-screw thread'.

As described above, the sizes of the first screw thread 11 and the second screw thread 21 vary due to the quality of bones into which they are respectively implanted. For example, the first portion 10 that is implanted into the cortical bone 41 that is relatively hard includes a dense number of screw threads for concentration of stress in a contacting portion between the first portion 10 and the cortical bone 21, thereby uniformly distributing the entire stress to a peripheral bone tissue 40. On the other hand, the second portion 20 inserted into the cancellous bone 42, which is relatively soft, is formed with a size that increases an amount of bone tissue being captured to thus obtain sufficient fixing force.

An outer diameter $D_{22}$ of a lower side of the second screw thread 21 is smaller than an outer diameter $D_{21}$ of an upper side thereof. The outer diameters may continuously increase upward, but the present invention is not limited thereto, and the outer diameters may discontinuously increase upward. As described above, the outer diameter $D_{22}$ of the lower side of the second screw thread 21 and the outer diameter $D_{21}$ of the upper side thereof are different from each other in order to apply a pressure to the cancellous bone 42 due to an increase in the outer diameters during a process of inserting the second portion 20 into the cancellous bone 42, thereby obtaining sufficient fixing force.

In this regard, the second portion 20 is formed tapering. More specifically, if an inclination angle between the central axis C and a first straight line $I_1$ that connects the second peaks 21a disposed in the upper and lower sides of the second screw thread 21 on a plane (refer to the cross-sectional shape of FIG. 5) passing through the central axis C is θ', θ' may be between 0.5° and 3°. If the inclination angle θ' between the central axis C and a first straight line $I_1$ is less than 0.5°, less pressure may be applied to the peripheral bone tissue 40 during the process of inserting the second screw thread 20. If the inclination angle θ' between the central axis C and a first straight line $I_1$ is greater than 3°, extreme pressure may be applied to the peripheral bone tissue 40, which causes damage to bones.

Also, both of the outer diameters the first portion 10 and the second portion 20 may be increased. More specifically, all the first peaks 11a of the first screw thread 11 and all the second peaks 21a of the second screw thread 21 may be disposed on the same plane.

If a width of the first roots 11b of the first screw thread 11 is d' and a width of the second roots 21b of the second screw thread 21 is d, d may be less than d. If d' is greater than d, the number of screw threads formed in the first screw thread 11 is less than that of the second screw thread 21, and thus the first portion 10 cannot achieve sufficient supporting force after implantation.

Also, if a vertical distance between one of the first roots 11b of the first screw thread 11 and the first peak 11a adjacent to the first root 11b is b', b' may be greater than 0.20 mm, and may be preferably greater than 0.25 mm. If b' is smaller than 0.20 mm, the size of the first screw thread 11 is extremely small, and thus supporting force between the peripheral bone tissue 40 and the first screw thread 11 can deteriorate.

Further, the distances the first screw thread 11 and the second screw thread 21 move per one rotation along the central axis are set to be the same. If the distances they move along the central axis are different, a greater rotational torque is required during implantation, and this may apply a strong pressure to the peripheral bone tissue 40 and cause cracks therein. The moving distance may be between 0.5 and 2.5 mm.

An inner diameter (or a bone diameter; $D_{23}$) of the second screw thread 21 may be smaller than an inner diameter $D_{13}$ of the first screw thread 11, preferably by 0.1 and 1.5 mm. The number of lines of the first screw thread 11 per lead (a distance that a peak of a screw thread moves in the central axis direction C when the implant fixture 1 makes one rotation with respect to the peak) may be greater than that of the second screw thread 21 per lead, preferably by more than 200%. More specifically, if the second screw thread 21 has one line, the first screw thread 11 may have two or more lines, and if the second screw thread 21 has two lines, the first screw thread 11 may have four or more lines.

A second cutting portion 22 is formed in the second screw thread 21 of the second portion 20. The second cutting portion 22 extends from the lower side of the second portion 20 to the upper side thereof. The second cutting portion 22 extends upward and is not parallel to the central axis C, unlike a first cutting portion 32 of the third portion 30 that will be described. Specifically, the second cutting portion 22 has an inclined shape, and, more specifically, coils in spiral form and extends upward. The second cutting portion 22 formed in the second screw thread 22 can facilitate an insertion from the third portion 30 to the second portion 20. That is, unlike the conventional art, the outer diameter of the second portion 20 increases upward, which slightly increases a torque during a process of inserting the second portion 20 into the peripheral bone tissue 40. The formation of the second cutting portion 22 facilitates inserting the second portion 20.

The maximum depth of the second cutting portion 22 may be less than a vertical distance (a height of the second screw thread 21; b) from one of the second peaks 21a of the second screw thread 21 and the second roots 21b adjacent to the second peak 21a, and more preferably, by 0.5 and 1.0 times. When the minimum depth of the second cutting portion 22 is smaller than 0.5 times the height of the second screw thread 21, a cutting effect is reduced, and when the minimum depth of the second cutting portion 22 is greater than 0.8 times the height of the second screw thread 21, the second cutting portion 22 may not sufficiently smooth the peripheral bone tissue 40.

The second screw thread 21 has a sharp screw thread shape, compared to the conventional art, and preferably a cutting edge shape.

More specifically, the shortest distance a (refer to FIG. 5) between the adjacent second roots 21b of the second screw thread 21 may be less than the vertical distance (the height of the second screw thread 21; b) from the second peaks 21a of the second screw thread 21 to the second roots 21b adjacent to the second peak 21a, more preferably, b/a (i.e. height/width) is between 0.9 and 1.5. That is, the height is greater than the width so that the second screw thread 21 has a sharp shape like a blade as a whole. Thus, when the second screw thread 21 rotates, the peripheral bone tissue 40 is easily cut and the implant fixture 1 is inserted into the peripheral bone tissue 40. Meanwhile, if b/a is less than 0.9, the second screw thread 21 is stumpy or is not sharp, and thus a sufficient cutting effect is not obtained, and if b/a is greater than 1.5, the second screw thread 21 is extremely thin and has a low strength, and thus a somewhat strong bone tissue is likely to easily damage the second screw thread 21 when rotating.

In addition, with regard to the cross-sectional shape of the second screw thread 21, if a width of a top of the second peaks 21a of the second screw thread 21 is c, and a width of the second roots 21b adjacent to the second peaks 21a is d, c may be less than d, more preferably, c:d is 1:2~1:6, and most preferably, c:d is 1:3~1:5 (refer to FIG. 5). With regard to a screw angle, if an angle between a straight line vertical to the central axis C and an inclination surface of the second screw thread 21 is θ, θ may be 5°~35°, and most preferably, 15°~20° (refer to FIG. 5). The screw thread can have a sufficient sharp shape of the above ratio of c:d and the above range of θ.

The first screw thread 11 and the second screw thread 21 may be continuously connected to each other. More specifically, as shown in FIG. 3, the second screw thread 21 is continuously connected to the first screw thread 11, and the first screw thread 11 is continuously connected to the second screw thread 21. The continuous connection of the first screw thread 11 and the second screw thread 21 can result in a natural implantation of the implant fixture 1 without an instant increase in implantation torque.

The third portion 30 is disposed in a lower side of the second portion 20, and includes a third screw thread 31 having an outer surface on which third peaks 31a and third roots 31b alternate with one another, and the first cutting portion 32 caved approaching the central axis C. The third portion 30 is the lowest end of the implant fixture 1 and is an entrance portion that is implanted into a bone tissue 40 at an initial stage. More specifically, the third portion 30 is inserted into the bone tissue 40 at an initial stage to form a female screw thread inside the bone tissue 40. The first cutting portion 32 that is deeply caved enables the third portion 30 to be easily inserted into the bone tissue 40.

The first cutting portion 32 vertically extends upward from a lower end of the third portion 30. More specifically, the first cutting portion 32 extends upward in parallel to the central axis C. The first cutting portion 32 is caved in deeper than the third roots 31b so that the first cutting portion 32 easily cuts a peripheral bone tissue of an implant hole located at a lower end of the implant fixture 1.

The shapes of the first cutting portion 32 and the second cutting portion 22 vary in order to improve surface roughness of the peripheral bone tissue 40 by minutely cutting the peripheral bone tissue 40, which has been roughly cut using the first cutting portion 32, with the second cutting portion 22. That is, as the second cutting portion 22 rotates, the peripheral bone tissue 40 that has been cut roughly using the first cutting portion 32 may be smoothed.

The dental implant fixture 1 according to the current embodiment of the present invention has the following effects. First, as illustrated in a left side of FIG. 6, an implant hole having a diameter h1 is formed in the bone tissue 40 with a drill so as to insert the implant fixture 1 in the implant hole. In detail, the dental implant fixture 1 is inserted into the implant hole while rotating around the central axis C. In this regard, the first cutting portion 32 disposed in the lowest end of the dental implant fixture 1 forms a female screw groove in the peripheral bone tissue 40, and simultaneously the third portion 30 is inserted into the implant hole at the same time. After the first cutting portion 32 is inserted, the second cutting portion 22 is inserted, thereby cutting and smoothing the bone tissue 40 and smoothing the peripheral bone tissue 40 at the same time. After the second portion 20 is completely inserted, the first portion 10 is inserted, and here, a cutting edge formed in the lowest end of the first portion 10 cuts the peripheral bone tissue such that the first portion 10 is easily inserted into the implant hole. The implant fixture 1 that is completely inserted into the bone tissue is shown in a right side of FIG. 6.

Also, the outer diameter of the second screw thread 21 increases upward so that a pressure applied to the peripheral bone tissue 40 gradually increases upward. Therefore, when the implant fixture 1 is inserted, the pressure is applied to the cancellous bone 42, thereby increasing fixing force. Further, the fixing force regarding the cancellous bone 42 is maintained, and, at the same time, a partially concentrated stress regarding each screw thread is distributed, bone absorption is prevented, and osseointegration is improved.

FIG. 7 is a schematic view illustrating the implant fixture 1 of FIG. 2, being implanted into the bone tissue 40 when an implant hole having a diameter h2 smaller than the diameter h1 of the implant hole of FIG. 6 is formed. In the conventional implant fixture having a stumpy screw thread as a whole, it is difficult to insert the conventional implant fixture into the implant hole having the small diameter h2. This is because an excessive implantation torque is required. If the conventional implant fixture is excessively inserted into the implant hole having the small diameter h2, a crack may occur in a bone tissue. Thus, it is necessary to additionally broaden the diameter h2 of the implant hole using a drill.

Also, since the implant fixture 1 of the present embodiment has a sharp screw thread as a whole, the implant fixture 1 easily cuts the peripheral bone tissue 40 like a drill blade when the screw thread rotates, thereby easily inserting the implant fixture 1 in the implant hole. That is, it is unnecessary to broaden the diameter h2 of the implant hole. The implant fixture 1 can obtain the same fixing force as that of an initial stage regardless of a diameter of a drill hole by reducing the sensitivity of the implant hole, and, in particular, can be sufficiently implanted into the implant hole owing to a sharp shape even if the implant hole has a small diameter.

Further, referring to FIG. 8, when an implant hole is formed in a direction different from a desired direction, if the implant fixture 1 is inserted into the implant hole after placing the implant fixture 1 in the desired direction, without forming a new implant hole in the desired direction, the implant fixture 1 can be implanted in the desired direction while the screw thread in the sharp shape cuts the peripheral bone tissue 40. That is, it is advantageously unnecessary to form a new implant hole.

According to the present embodiment, a concentrated stress to the cortical bone 41 is spread to the cancellous bone 42 so as to uniformly distribute the stress to the implant fixture 1 as a whole, thereby preventing bone absorption of the cortical bone 41 and improving osseointegration.

The present invention has the following modification.

Figure 9:
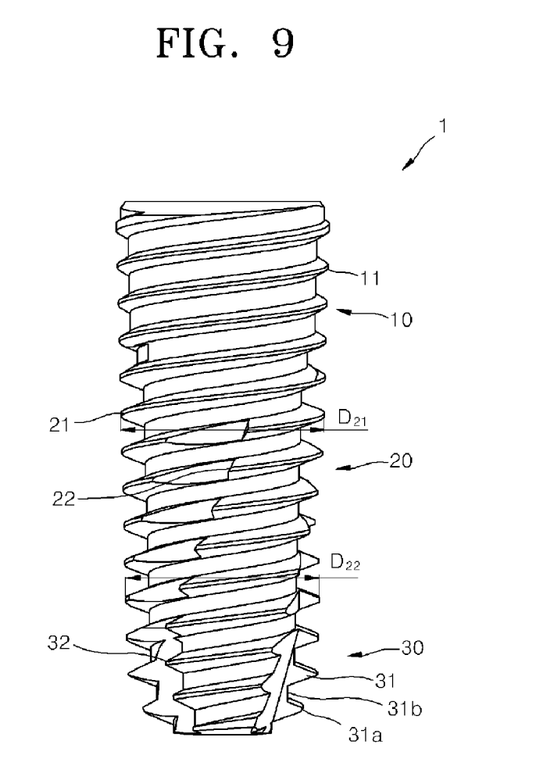
FIG. 9 illustrates an implant fixture according to another embodiment of the present invention.
Figure 10:
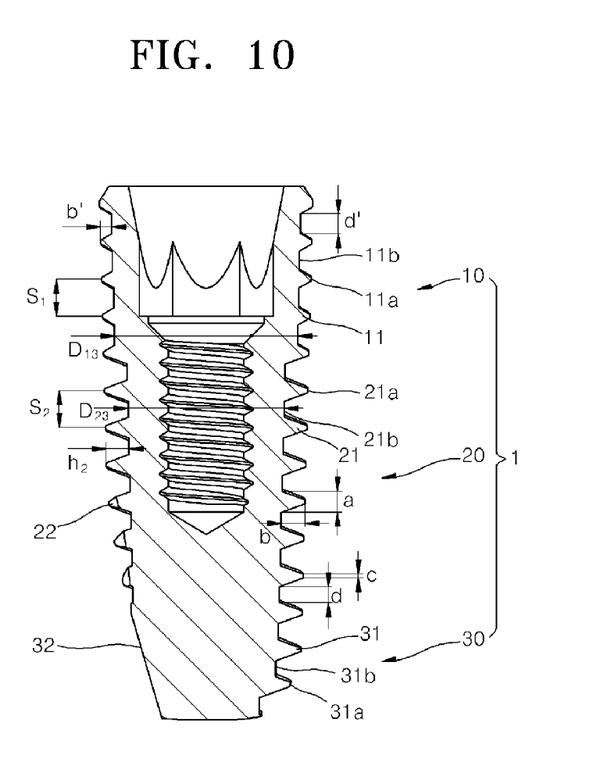
FIG. 10 is a cross-sectional view of the implant fixture of FIG. 9.

FIG. 9 illustrates an implant fixture 1 according to another embodiment of the present invention, and FIG. 10 is a cross-sectional view of the implant fixture of FIG. 9.

Although the distances $S_1$ between the adjacent first peaks 11a of the first screw thread 11 and the distances $S_2$ between the adjacent second peaks 21a of the second screw thread 21 are different from each other in the previous embodiment, the distances $S_1$ and the distances $S_2$ are the same in the present embodiment. In this regard, the width d' of the first roots 11b of the first screw thread 11 may be between 0.3 mm~0.6 mm. The distances $S_1$ and the distances $S_2$ are the same, and the width d' of the first roots 11b is maintained within a predetermined range in order to produce a sufficient roughness since powders having fine sizes (generally diameters between 0.25 mm~0.5 mm) used for a surface treatment obtain a sufficient bone width in the second portion 20, thereby sufficiently contacting the second roots 21b. Meanwhile, if a bone width of the first portion 10 is small like the conventional art, since the width d' of the first roots 11b is narrow, the powders have difficulties in sufficiently contacting the bone surface. However, in the present embodiment, the distances $S_1$ and the distances $S_2$ are the same, and the width d' of the first roots 11b is maintained within a predetermined range so as to obtain a sufficient width of the first roots 11b, so that the powders can sufficiently contact the surface of the first roots 11b. If the surface roughness is sufficiently obtained, a junction between the implant fixture and the peripheral bone tissue increases.

Further, the distances $S_1$ and $S_2$ may be between 0.6 mm~1.0 mm, more preferably, 0.7 mm~0.9 mm, and most preferably, 0.8 mm. The implant fixture of the present embodiment is similar to the implant fixture 1 described with reference to FIG. 2 in terms of function and structure, and thus the detailed description will not be repeated.

In the previous embodiment, although the width d' of the first roots 11b of the first screw thread 11 is less than the width d of the second roots 21b of the second screw thread 21, the widths d' and d may be the same.

While this invention has been particularly shown and described with reference to embodiments thereof, it will be understood by those of ordinary skill in the art that various changes in form and details may be made therein without departing from the spirit and scope of the invention as defined by the appended claims. The embodiments should be considered in descriptive sense only and not for purposes of limitation. Therefore, the scope of the invention is defined not by the detailed description of the invention but by the appended claims, and all differences within the scope will be construed as being included in the present invention.

The invention claimed is:

1. A dental implant fixture that is inserted into a bone tissue formed of a cortical bone and a cancellous bone by rotating about a central axis to thereby form an artificial tooth root, comprising:
   a first portion that is inserted into the cortical bone and comprises a first screw thread having first peaks and first roots alternating with one another on an outer surface of the first portion;
   a second portion that is disposed below the first portion, is inserted into the cancellous bone, and comprises a second screw thread having second peaks and second roots alternating with one another on an outer surface of the second portion, wherein the cross section of the second screw thread is greater than the cross section of the first screw thread, and wherein a separation distance between adjacent second peaks of the second screw thread is the same as a separation distance between adjacent first peaks of the first screw thread; and
   a third portion that is disposed below the second portion, is inserted into the cancellous bone, and comprises a third screw thread having third peaks and third roots alternating with one another on an outer surface of the third portion, and a first cutting portion that is caved closer to a central axis than the third roots,
   wherein an outer diameter of second peaks decreases gradually from an upper side of the second portion to an lower side of the second portion over the entire length of the second portion, wherein the first screw thread and the second screw thread are continuously connected to each other, wherein the second screw thread of the second portion comprises a second cutting portion that extends upward not in parallel to the central axis and is caved toward the central axis, and wherein the maximum depth of the second cutting portion is less than a vertical distance from one of the second peaks of the second screw thread and the second roots adjacent to the second peak, and the second cutting portion is connected to the first cutting portion.

2. The dental implant fixture of claim 1, wherein an inner diameter of the second screw thread is smaller than that of the first screw thread.

3. The dental implant fixture of claim 2, wherein the inner diameter of the second screw thread is smaller than that of the first screw thread by 0.1 mm~1.5 mm.

4. The dental implant fixture of claim 1, wherein all the first peaks of the first screw thread and all the second peaks of the second screw thread lie on a plane inclined to the central axis.

5. The dental implant fixture of claim 1, wherein the width of the first roots of the first screw thread is between 0.3 mm~0.6 mm.

6. The dental implant fixture of claim 1, wherein, if an inclination angle between the central axis and a first straight line that connects the second peaks disposed in the upper and lower sides of the second screw thread on a plane passing through the central axis is θ', θ' is between 0.5° and 3°.

7. The dental implant fixture of claim 1, wherein the first screw thread and the second screw thread are a plurality of screw threads.

8. The dental implant fixture of claim 1, wherein, if distances between the adjacent first peaks of the first screw thread are $S_1$, and distances between the adjacent second peaks of the second screw thread are $S_2$, $S_1$ and $S_2$ are between 0.6 mm~1.0 mm.

9. The dental implant fixture of claim 1, wherein, if a vertical distance between one of the first roots of the first screw thread and the first peak adjacent to the first roots is b', b' is greater than 0.20 mm.

10. The dental implant fixture of claim 1, wherein the first screw thread and the second screw thread have the same moving distance per rotation in a direction of the central axis.

11. The dental implant fixture of claim 10, wherein the moving distance is between 0.5 mm~2.5 mm.

12. The dental implant fixture of claim 1, wherein the first cutting portion extends upward in parallel to the central axis.

13. The dental implant fixture of claim 1, wherein the second cutting portion is inclined upward.

14. The dental implant fixture of claim 1, wherein, if the shortest distance between the adjacent second roots of the second screw thread is a, and the vertical distance from one of the second peaks of the second screw thread and the second roots adjacent to the second peak is b, a is less than b.

15. The dental implant fixture of claim 1, wherein, if a width of a top of the second peaks of the second screw thread is c, and a width of the second roots adjacent to the second peaks is d, c is less than d.

16. The dental implant fixture of claim 1, wherein, if an angle between a straight line vertical to the central axis and an inclination surface of the second screw thread is θ, θ is between 5°~35°.

17. A dental implant fixture that is inserted into a bone tissue formed of a cortical bone and a cancellous bone by rotating about a central axis to thereby form an artificial tooth root, comprising:

a first portion that is inserted into the cortical bone and comprises a first screw thread having first peaks and first roots alternating with one another on an outer surface of the first portion;

a second portion that is disposed below the first portion, is inserted into the cancellous bone, and comprises a second screw thread having second peaks and second roots alternating with one another on an outer surface of the second portion, wherein the cross section of the second screw thread is greater than the cross section of the first screw thread, and wherein a separation distance between adjacent second peaks of the second screw thread is the same as a separation distance between adjacent first peaks of the first screw thread; and a third portion that is disposed below the second portion, is inserted into the cancellous bone, and comprises a third screw thread having third peaks and third roots alternating with one another on an outer surface of the third portion, and a first cutting portion that is caved closer to a central axis than the third roots, wherein an outer diameter of second peaks decreases gradually from an upper side of the second portion to an lower side of the second portion over the entire length of the second portion, wherein the first screw thread and the second screw thread are continuously connected to each other, wherein, if the width of the first roots of the first screw thread is d', and the width of the second roots of the second screw thread is d, d' is the same as d, wherein the second screw thread of the second portion comprises a second cutting portion that extends upward not in parallel to the central axis and is caved toward the central axis, and wherein the maximum depth of the second cutting portion is less than a vertical distance from one of the second peaks of the second screw thread and the second roots adjacent to the second peak, wherein the second cutting portion is connected to the first cutting portion.

* * * * *